United States Patent
Buttermann

(10) Patent No.: US 9,204,899 B2
(45) Date of Patent: *Dec. 8, 2015

(54) SEGMENTAL ORTHOPEDIC DEVICE FOR SPINAL ELONGATION AND FOR TREATMENT OF SCOLIOSIS

(71) Applicant: DYNAMIC SPINE, LLC, Mahtomedi, MN (US)

(72) Inventor: Glenn R Buttermann, Mahtomedi, MN (US)

(73) Assignee: Dynamic Spine, LLC, Mahtomedi, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/444,860

(22) Filed: Jul. 28, 2014

(65) Prior Publication Data

US 2014/0336705 A1    Nov. 13, 2014

Related U.S. Application Data

(63) Continuation of application No. 12/149,403, filed on Apr. 30, 2008, now Pat. No. 8,790,380.

(60) Provisional application No. 60/935,098, filed on Jul. 26, 2007.

(51) Int. Cl.
  *A61B 17/70* (2006.01)
  *A61B 17/66* (2006.01)

(52) U.S. Cl.
  CPC ........... *A61B 17/7047* (2013.01); *A61B 17/707* (2013.01); *A61B 17/66* (2013.01); *A61B 17/7001* (2013.01)

(58) Field of Classification Search
  CPC .......... A61B 17/7001; A61B 17/7002; A61B 17/7032; A61B 17/7035; A61B 17/7046; A61B 17/7047; A61B 17/7049; A61B 17/7056
  USPC ............... 606/60, 75, 151, 246, 250–253, 606/264–267, 272, 276–279, 300, 324; 24/502, 514; 403/60, 67–73, 77–79, 403/150–159, 161, 164, 165, 373, 403/374.1–374.4; 269/143, 249, 95; 29/276, 257
  See application file for complete search history.

(56) References Cited

U.S. PATENT DOCUMENTS

| | | | |
|---|---|---|---|
| 945,213 A * | 1/1910 | Blackburn | ................ 248/217.2 |
| 1,766,546 A | 6/1930 | Roos | |
| 2,537,322 A | 1/1951 | Wazenberg | |
| 2,543,550 A | 2/1951 | Kneeland | |
| 2,589,520 A | 3/1952 | Wallenius | |

(Continued)

FOREIGN PATENT DOCUMENTS

| | | |
|---|---|---|
| DE | 28 21 678 A1 | 11/1979 |
| FR | 2782911 A | 3/2000 |
| FR | 2892617 A | 5/2007 |
| WO | WO-90/12553 A | 11/1990 |
| WO | WO-93/25161 A | 12/1993 |

(Continued)

OTHER PUBLICATIONS

Supplementary European Search Report in corresponding European Application No. 11793147.7 dated Oct. 10, 2014, 7 pages.

(Continued)

*Primary Examiner* — Eduardo C Robert
*Assistant Examiner* — Michelle C Eckman
(74) *Attorney, Agent, or Firm* — Foley & Lardner LLP

(57) ABSTRACT

An orthopaedic device to realign bone segments comprises first and second attachment members and a spacer member. The first attachment member is attached to a first rib bone or first transverse process of a vertebra. The second attachment member is attached to a second rib bone or second transverse process of a vertebra adjacent to the first rib bone or the first transverse process. The spacer member is positioned between the first and second attachment members. The spacer member provides distraction between the first and second rib bones or transverse processes to realign the rib bones. The spacer member is releasably connected to the first and second attachment members. The attachment members comprise a clamp and screw combination.

19 Claims, 10 Drawing Sheets

(56) References Cited

U.S. PATENT DOCUMENTS

| | | | |
|---|---|---|---|
| 2,722,440 A | 11/1955 | Barton | |
| 2,824,913 A | 2/1958 | Taylor | |
| 4,085,744 A * | 4/1978 | Lewis et al. | 623/17.11 |
| 4,361,141 A * | 11/1982 | Tanner | 606/252 |
| 4,364,381 A | 12/1982 | Sher et al. | |
| 4,409,968 A * | 10/1983 | Drummond | 606/86 A |
| 4,411,259 A * | 10/1983 | Drummond | 606/86 A |
| 4,422,451 A * | 12/1983 | Kalamchi | 606/276 |
| 4,531,522 A | 7/1985 | Bedi et al. | |
| 4,611,582 A * | 9/1986 | Duff | 606/258 |
| 4,619,447 A | 10/1986 | Blake | |
| 4,702,447 A * | 10/1987 | Westwood, III | 248/231.51 |
| 4,823,636 A | 4/1989 | Suska | |
| 4,852,841 A | 8/1989 | Sebring | |
| 4,901,964 A | 2/1990 | McConnell | |
| 4,950,270 A | 8/1990 | Bowman et al. | |
| 5,007,909 A * | 4/1991 | Rogozinski | 606/277 |
| 5,030,235 A | 7/1991 | Campbell, Jr. | |
| 5,074,864 A * | 12/1991 | Cozad et al. | 606/54 |
| 5,096,150 A * | 3/1992 | Westwood | 248/231.51 |
| 5,112,332 A * | 5/1992 | Cozad et al. | 606/279 |
| 5,116,334 A * | 5/1992 | Cozad et al. | 606/250 |
| 5,147,359 A * | 9/1992 | Cozad et al. | 606/276 |
| 5,190,543 A | 3/1993 | Schlapfer | |
| 5,261,908 A | 11/1993 | Campbell, Jr. | |
| 5,290,289 A | 3/1994 | Sanders et al. | |
| 5,330,472 A * | 7/1994 | Metz-Stavenhagen | 606/53 |
| 5,334,203 A * | 8/1994 | Wagner | 606/252 |
| 5,344,422 A | 9/1994 | Frigg | |
| 5,352,225 A * | 10/1994 | Yuan et al. | 606/324 |
| 5,380,326 A * | 1/1995 | Lin | 606/330 |
| 5,413,576 A | 5/1995 | Rivard | |
| 5,415,659 A * | 5/1995 | Lee et al. | 606/276 |
| 5,423,857 A * | 6/1995 | Rosenman et al. | 606/219 |
| 5,507,747 A * | 4/1996 | Yuan et al. | 606/276 |
| 5,520,689 A | 5/1996 | Schlapfer et al. | |
| 5,586,983 A * | 12/1996 | Sanders et al. | 606/277 |
| 5,630,816 A * | 5/1997 | Kambin | 606/252 |
| 5,632,744 A * | 5/1997 | Campbell, Jr. | 606/250 |
| 5,662,648 A | 9/1997 | Faccioli et al. | |
| 5,676,665 A | 10/1997 | Bryan | |
| 5,688,273 A * | 11/1997 | Errico et al. | 606/276 |
| 5,688,274 A * | 11/1997 | Errico et al. | 606/276 |
| 5,689,864 A | 11/1997 | White | |
| 5,697,650 A | 12/1997 | Brown | |
| 5,733,284 A * | 3/1998 | Martin | 606/248 |
| 5,800,548 A * | 9/1998 | Martin et al. | 606/253 |
| 6,053,917 A | 4/2000 | Sherman et al. | |
| 6,136,000 A | 10/2000 | Louis et al. | |
| 6,352,537 B1 | 3/2002 | Strnad | |
| 6,375,656 B1 | 4/2002 | Faure | |
| 6,387,097 B1 | 5/2002 | Alby | |
| 6,547,789 B1 * | 4/2003 | Ventre et al. | 606/308 |
| 6,589,243 B1 | 7/2003 | Viart et al. | |
| 6,626,909 B2 | 9/2003 | Chin | |
| 6,660,007 B2 | 12/2003 | Khanna | |
| 6,719,795 B1 | 4/2004 | Cornwall et al. | |
| 6,860,884 B2 | 3/2005 | Shirado et al. | |
| 6,926,242 B2 * | 8/2005 | Hall | 248/230.4 |
| 7,011,659 B2 | 3/2006 | Lewis et al. | |
| 7,029,472 B1 | 4/2006 | Fortin | |
| 7,137,986 B2 | 11/2006 | Troxell et al. | |
| 7,249,399 B2 | 7/2007 | Taylor | |
| 7,264,620 B2 | 9/2007 | Taylor | |
| 7,338,490 B2 | 3/2008 | Ogilvie et al. | |
| 7,614,173 B2 | 11/2009 | Kim | |
| 7,635,365 B2 | 12/2009 | Ellis et al. | |
| 7,666,210 B2 * | 2/2010 | Franck et al. | 606/250 |
| 7,695,501 B2 | 4/2010 | Ellis et al. | |
| 7,703,358 B2 * | 4/2010 | Ubinana Felix | 81/487 |
| 7,713,284 B2 | 5/2010 | Crofford | |
| 7,717,938 B2 | 5/2010 | Kim et al. | |
| 7,883,532 B2 * | 2/2011 | Biscup et al. | 606/324 |
| 7,901,436 B2 | 3/2011 | Baccelli | |
| 7,922,746 B2 | 4/2011 | Miller | |
| 7,927,355 B2 | 4/2011 | Berrevoets et al. | |
| 7,927,357 B2 * | 4/2011 | Sacher et al. | 606/258 |
| 7,942,908 B2 * | 5/2011 | Sacher et al. | 606/258 |
| 7,966,703 B2 | 6/2011 | Ubinana Felix | |
| 7,980,521 B2 | 7/2011 | Harr et al. | |
| 8,025,678 B2 | 9/2011 | Reynolds et al. | |
| 8,025,683 B2 | 9/2011 | Morrison | |
| 8,043,337 B2 | 10/2011 | Klyce et al. | |
| 8,048,166 B2 | 11/2011 | Brown et al. | |
| 8,051,515 B1 | 11/2011 | Kring | |
| 8,057,472 B2 | 11/2011 | Walker et al. | |
| 8,075,597 B2 | 12/2011 | Stahurski et al. | |
| 8,080,037 B2 | 12/2011 | Butler et al. | |
| 8,080,046 B2 | 12/2011 | Suddaby | |
| 8,083,780 B2 | 12/2011 | Mcclellan et al. | |
| 8,105,366 B2 | 1/2012 | Null et al. | |
| 8,172,875 B2 | 5/2012 | Taylor | |
| 8,172,882 B2 | 5/2012 | Klyce et al. | |
| 8,172,887 B2 | 5/2012 | Gabele | |
| 8,177,823 B2 | 5/2012 | Lake et al. | |
| 8,197,515 B2 | 6/2012 | Levy et al. | |
| 8,197,543 B2 | 6/2012 | Wang | |
| 8,226,689 B2 | 7/2012 | Jones et al. | |
| 8,231,655 B2 | 7/2012 | Stinson et al. | |
| 8,241,334 B2 | 8/2012 | Butler et al. | |
| 8,246,660 B2 | 8/2012 | Boris et al. | |
| 8,292,924 B2 | 10/2012 | Neary et al. | |
| 8,298,275 B2 | 10/2012 | Rezach | |
| 8,313,514 B2 | 11/2012 | Puno | |
| 8,430,917 B2 | 4/2013 | Rezach | |
| 8,790,380 B2 * | 7/2014 | Buttermann | 606/324 |
| 8,915,962 B1 * | 12/2014 | Suddaby | 623/17.11 |
| 2002/0013585 A1 | 1/2002 | Gournay et al. | |
| 2002/0019633 A1 * | 2/2002 | Ray | 606/53 |
| 2002/0095156 A1 | 7/2002 | Kuras et al. | |
| 2002/0169451 A1 | 11/2002 | Yeh | |
| 2003/0004511 A1 * | 1/2003 | Ferree | 606/61 |
| 2003/0032959 A1 | 2/2003 | Yeh | |
| 2003/0045876 A1 * | 3/2003 | Stahurski | 606/61 |
| 2003/0080267 A1 | 5/2003 | Eslick | |
| 2003/0083659 A1 | 5/2003 | Lin et al. | |
| 2003/0088251 A1 | 5/2003 | Braun et al. | |
| 2003/0109881 A1 * | 6/2003 | Shirado et al. | 606/61 |
| 2003/0109882 A1 | 6/2003 | Shirado et al. | |
| 2003/0125738 A1 | 7/2003 | Khanna | |
| 2003/0125740 A1 | 7/2003 | Khanna | |
| 2003/0130659 A1 * | 7/2003 | Haider | 606/61 |
| 2003/0187437 A1 * | 10/2003 | Ginsburg | 606/61 |
| 2004/0030388 A1 | 2/2004 | Null et al. | |
| 2004/0055429 A1 | 3/2004 | Winkler | |
| 2004/0064140 A1 | 4/2004 | Taylor et al. | |
| 2004/0087948 A1 | 5/2004 | Suddaby | |
| 2004/0111091 A1 | 6/2004 | Ogilvie et al. | |
| 2004/0186472 A1 * | 9/2004 | Lewis et al. | 606/61 |
| 2005/0131412 A1 * | 6/2005 | Olevsky et al. | 606/69 |
| 2005/0171539 A1 | 8/2005 | Braun et al. | |
| 2005/0228377 A1 | 10/2005 | Chao et al. | |
| 2005/0251138 A1 | 11/2005 | Boris et al. | |
| 2005/0267475 A1 | 12/2005 | Miller, III | |
| 2005/0267480 A1 | 12/2005 | Suddaby | |
| 2005/0273100 A1 | 12/2005 | Taylor | |
| 2006/0036241 A1 | 2/2006 | Siegal | |
| 2006/0058790 A1 | 3/2006 | Carl et al. | |
| 2006/0084990 A1 | 4/2006 | Gournay et al. | |
| 2006/0116687 A1 | 6/2006 | Miller et al. | |
| 2006/0155279 A1 | 7/2006 | Ogilvie | |
| 2006/0229615 A1 | 10/2006 | Abdou | |
| 2006/0229616 A1 | 10/2006 | Albert et al. | |
| 2006/0235391 A1 * | 10/2006 | Sutterlin, III | 606/61 |
| 2006/0241601 A1 | 10/2006 | Trautwein et al. | |
| 2006/0247626 A1 | 11/2006 | Taylor et al. | |
| 2006/0271193 A1 | 11/2006 | Hartmann et al. | |
| 2006/0293663 A1 | 12/2006 | Walkenhorst et al. | |
| 2007/0016189 A1 * | 1/2007 | Lake et al. | 606/61 |
| 2007/0072459 A1 * | 3/2007 | Stahurski et al. | 439/135 |
| 2007/0083201 A1 | 4/2007 | Jones et al. | |
| 2007/0118118 A1 | 5/2007 | Kwak et al. | |
| 2007/0123883 A1 * | 5/2007 | Ellis et al. | 606/69 |
| 2007/0225713 A1 * | 9/2007 | Altarac et al. | 606/64 |

(56) References Cited

U.S. PATENT DOCUMENTS

| | | | |
|---|---|---|---|
| 2007/0239161 A1* | 10/2007 | Giger et al. | 606/61 |
| 2007/0276384 A1* | 11/2007 | Spratt | 606/72 |
| 2008/0033436 A1 | 2/2008 | Song et al. | |
| 2008/0077144 A1 | 3/2008 | Crofford | |
| 2008/0103512 A1* | 5/2008 | Gately | 606/151 |
| 2008/0114401 A1 | 5/2008 | Liu et al. | |
| 2008/0177315 A1 | 7/2008 | Usher | |
| 2008/0228225 A1 | 9/2008 | Trautwein et al. | |
| 2008/0234733 A1* | 9/2008 | Scrantz et al. | 606/246 |
| 2008/0234766 A1* | 9/2008 | Henderson et al. | 606/86 B |
| 2008/0294200 A1 | 11/2008 | Kohm et al. | |
| 2008/0306551 A1 | 12/2008 | Sanders et al. | |
| 2009/0018584 A1* | 1/2009 | Henderson et al. | 606/246 |
| 2009/0030457 A1 | 1/2009 | Janowski et al. | |
| 2009/0030462 A1 | 1/2009 | Buttermann | |
| 2009/0062869 A1 | 3/2009 | Claverie et al. | |
| 2009/0105766 A1 | 4/2009 | Thompson et al. | |
| 2009/0112263 A1* | 4/2009 | Pool et al. | 606/246 |
| 2009/0118774 A1 | 5/2009 | Miller, III | |
| 2009/0118775 A1 | 5/2009 | Burke | |
| 2009/0163920 A1* | 6/2009 | Hochschuler et al. | 606/74 |
| 2009/0177230 A1* | 7/2009 | Henderson et al. | 606/246 |
| 2009/0198277 A1 | 8/2009 | Gordon et al. | |
| 2009/0248090 A1 | 10/2009 | Gordon et al. | |
| 2009/0270929 A1* | 10/2009 | Suddaby | 606/324 |
| 2009/0287253 A1* | 11/2009 | Felix et al. | 606/278 |
| 2010/0057127 A1 | 3/2010 | Mcguire et al. | |
| 2010/0069960 A1* | 3/2010 | Chaput | 606/249 |
| 2010/0094303 A1* | 4/2010 | Chang et al. | 606/90 |
| 2010/0121381 A1* | 5/2010 | Berta et al. | 606/264 |
| 2010/0137913 A1* | 6/2010 | Khatchadourian et al. | 606/258 |
| 2010/0152575 A1* | 6/2010 | Henderson et al. | 600/425 |
| 2010/0160979 A1* | 6/2010 | Tornier | 606/305 |
| 2010/0179597 A1* | 7/2010 | Henderson et al. | 606/264 |
| 2010/0198274 A1 | 8/2010 | Yeung et al. | |
| 2010/0217271 A1* | 8/2010 | Pool et al. | 606/90 |
| 2010/0222822 A1* | 9/2010 | Farris et al. | 606/264 |
| 2010/0241230 A1 | 9/2010 | Mazzuca et al. | |
| 2010/0249842 A1 | 9/2010 | Mir | |
| 2010/0274291 A1* | 10/2010 | McClellan et al. | 606/276 |
| 2010/0292739 A1 | 11/2010 | Schwab | |
| 2010/0305616 A1* | 12/2010 | Carbone | 606/264 |
| 2011/0106163 A1 | 5/2011 | Hochschuler et al. | |
| 2011/0111929 A1 | 5/2011 | Allison et al. | |
| 2011/0137353 A1* | 6/2011 | Buttermann | 606/305 |
| 2011/0144694 A1* | 6/2011 | Laeng et al. | 606/263 |
| 2011/0160779 A1 | 6/2011 | Schlaepfer et al. | |
| 2011/0178552 A1* | 7/2011 | Biscup et al. | 606/246 |
| 2011/0184463 A1 | 7/2011 | Schwend | |
| 2011/0251643 A1* | 10/2011 | Miladi | 606/254 |
| 2011/0257690 A1 | 10/2011 | Rezach | |
| 2011/0288592 A1 | 11/2011 | Mckinley | |
| 2011/0313323 A1* | 12/2011 | Henderson et al. | 600/594 |
| 2012/0016420 A1* | 1/2012 | Naraghi | 606/250 |
| 2012/0035656 A1* | 2/2012 | Pool et al. | 606/246 |
| 2012/0035661 A1* | 2/2012 | Pool et al. | 606/258 |
| 2012/0047690 A1 | 3/2012 | Ginocchio | |
| 2012/0083851 A1 | 4/2012 | Felix et al. | |
| 2012/0088380 A1 | 4/2012 | Smith | |
| 2012/0209328 A1* | 8/2012 | Alamin et al. | 606/248 |
| 2012/0271352 A1 | 10/2012 | Schulze et al. | |
| 2012/0271354 A1 | 10/2012 | Baccelli et al. | |
| 2012/0283780 A1 | 11/2012 | Ludwig et al. | |
| 2013/0041410 A1* | 2/2013 | Hestad et al. | 606/263 |
| 2013/0046352 A1* | 2/2013 | McClintock | 606/86 A |
| 2013/0131738 A1* | 5/2013 | Powell et al. | 606/324 |
| 2013/0184770 A1 | 7/2013 | Buttermann | |
| 2013/0218208 A1* | 8/2013 | Khoury | 606/278 |
| 2013/0231704 A1* | 9/2013 | Larroque-Lahitette | 606/277 |
| 2013/0274807 A1* | 10/2013 | Prajapati | 606/278 |
| 2013/0304129 A1* | 11/2013 | Hawkins et al. | 606/276 |
| 2014/0135853 A1* | 5/2014 | Reisberg | 606/324 |
| 2014/0214087 A1* | 7/2014 | Wahl et al. | 606/281 |
| 2014/0222074 A1* | 8/2014 | Rathbun et al. | 606/258 |
| 2014/0236234 A1* | 8/2014 | Kroll et al. | 606/264 |
| 2014/0257488 A1* | 9/2014 | Alheidt et al. | 623/17.16 |
| 2014/0277147 A1* | 9/2014 | Alexander et al. | 606/259 |
| 2014/0343612 A1* | 11/2014 | Rezach et al. | 606/276 |
| 2015/0025574 A1* | 1/2015 | Mackall | 606/246 |
| 2015/0032158 A1* | 1/2015 | Khajavi et al. | 606/246 |
| 2015/0032159 A1* | 1/2015 | Beger et al. | 606/265 |

FOREIGN PATENT DOCUMENTS

| | | |
|---|---|---|
| WO | WO-97/29707 A | 8/1997 |
| WO | WO-2004/019757 A2 | 3/2004 |
| WO | WO-2005/044152 A1 | 5/2005 |
| WO | WO-2011/133690 A2 | 10/2011 |
| WO | WO-2011/156573 A1 | 12/2011 |

OTHER PUBLICATIONS

Australian Office Action dated Jan. 15, 2014 received in corresponding AU Application No. 2011264818.
European Office Action dated Oct. 25, 2011 as received in corresponding European Patent Application No. 08743411.4, 5 pages.
European Office Action dated Sep. 23, 2010 as received in corresponding European Patent Application No. 08743411.4, 3 pages.
Final Office Action dated Aug. 14, 2013, as received in corresponding U.S. Appl. No. 13/028,161.
Final Office Action in U.S. Appl. No. 12/149,403 dated Apr. 26, 2013.
International Search Report and Written Opinion dated Jun. 29, 2012 as received in corresponding PCT Application No. PCT/US2012/024887.
International Search Report and Written Opinion dated Oct. 4, 2011 as received in corresponding PCT Application No. PCT/US2011/039760, 13 pages.
International Search Report and Written Opinion in PCT/US2013/027386 dated Apr. 26, 2013.
International Search Report mailed Nov. 12, 2008 in PCT/US2008/005532, 5 pages.
Kim, Won Joong, et al. "The Influence of Fixation Rigidity on Intervertebral Joints—An Experimental Comparison between a Rigid and a Flexible System", J Korean Neurosurg Soc, vol. 37, 2005, pp. 364-369.
Notice of Allowance received in related U.S. Appl. No. 12/149,403 dated Mar. 14, 2014.
Office Action received in connection with U.S. Appl. No. 13/028,161 dated Dec. 20, 2012.
Patent Examination Report received in connection with related Australian application No. AU2008279798 dtd Nov. 14, 2012.
US Notice of Allowance received Mar. 14, 2014.
US Office Action dated Aug. 10, 2011 as received in corresponding U.S. Appl. No. 12/149,403, 12 pages.
US Office Action dated Sep. 24, 2012 as received in corresponding U.S. Appl. No. 12/149,403.
US Office Action received in U.S. Appl. No. 12/149,403; Dtd Feb. 22, 2011.
Non-Final Office Action dated Aug. 19, 2014, received in U.S. Appl. No. 13/028,161.
Notice of Allowance issued in U.S. Appl. No. 13/028,161 dated Mar. 24, 2015.
Notice of Allowance in U.S. Appl. No. 13/702,854 dated Feb. 20, 2015.
Notice of Allowance dated Jun. 17, 2015 in U.S. Appl. No. 13/028,161, 11 pages.
Notice of Allowance dated Jun. 8, 2015, in U.S. Appl. No. 13/702,854, 9 pages.
Office Action issued in co-pending Canadian Application No. 2,694,437 mailed May 13, 2014.
Office Action issued in co-pending Canadian Patent Application No. 2,694,437 mailed Mar. 5, 2015.
Patent Examination Report No. 2 received in corresponding Australian Application No. 2011264818 mailed Mar. 5, 2015.
Patent Examination Report No. 1 dated Aug. 6, 2015, received in corresponding Australian application No. 2012217924, 7 pages.

* cited by examiner

Fig. 6
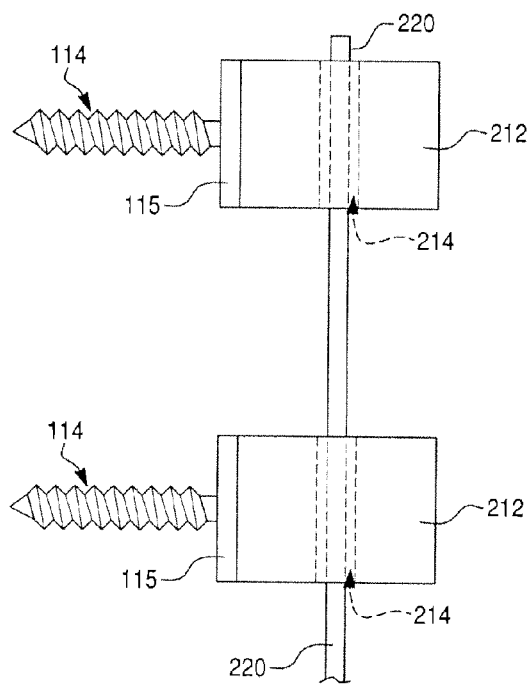
Fig. 7(a)  Fig. 7(b)  Fig. 7(c)
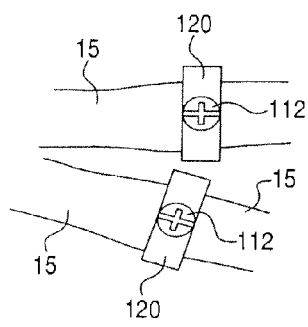 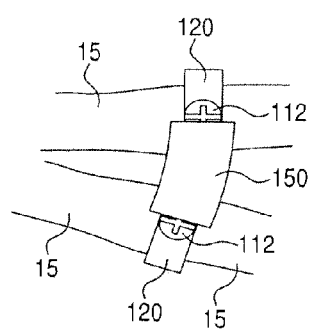 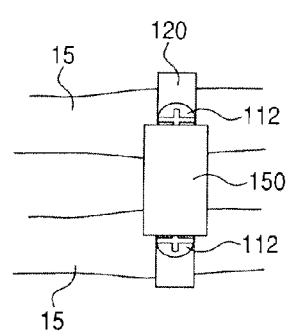

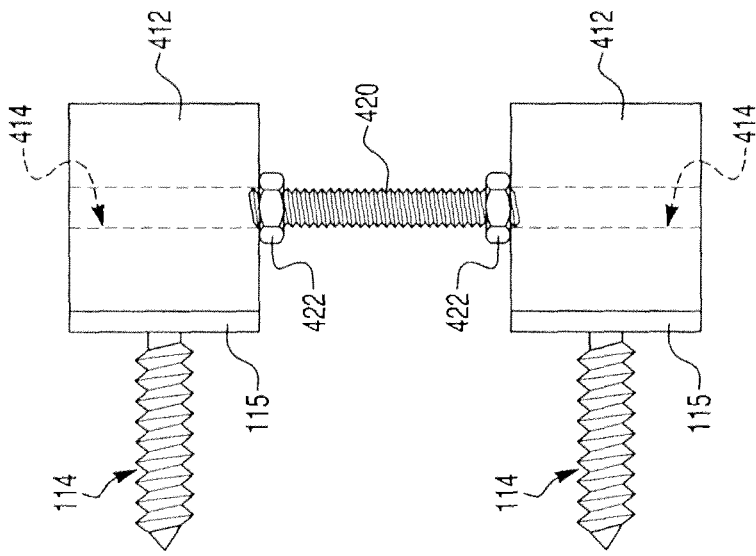
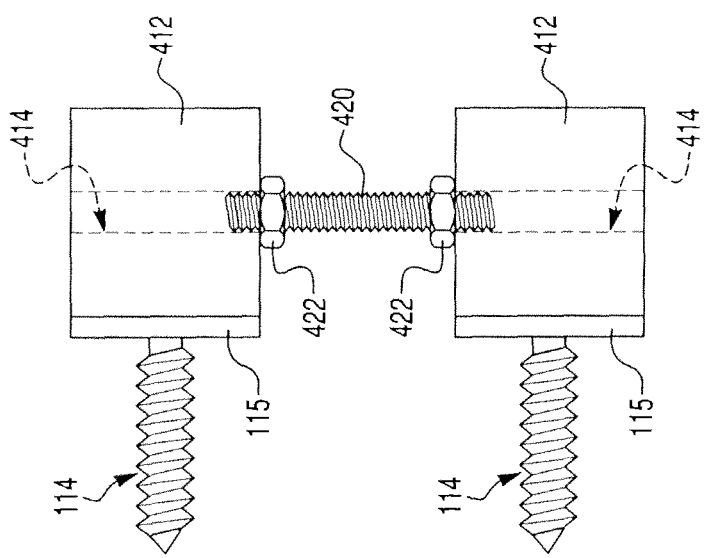

SEGMENTAL ORTHOPEDIC DEVICE FOR SPINAL ELONGATION AND FOR TREATMENT OF SCOLIOSIS

CROSS-REFERENCE TO RELATED PATENT APPLICATIONS

The present application claims a priority benefit, under 35 U.S.C. §120, as a continuation application of U.S. patent application Ser. No. 12/149,403, filed Apr. 30, 2008, entitled "SEGMENTAL ORTHOPEDIC DEVICE FOR SPINAL ELONGATION AND FOR TREATMENT OF SCOLIOSIS" and like that application, the present application claims priority to U.S. Provisional Application No. 60/935,098, filed Jul. 26, 2007, which applications are hereby incorporated herein by reference in their entireties.

BACKGROUND OF THE INVENTION

The present disclosure relates generally to orthopaedic devices. The present disclosure relates to orthopaedic devices for spinal elongation and for treatment of scoliosis.

External and internal fixators that are anchored to segments of bone have been used extensively over the last century. The fixators may be rigid or dynamic, and they may be expandable or apply distractive/compressive forces (longitudinal or at an angle) to realign bone segments. Historically these devices were most often used for trauma cases to stabilize fractures. Modern applications have also used them for extremity deformity, limb lengthening, and bone transport.

Orthopaedic devices can be segmental or non-segmental. Non-segmental devices typically have bone anchors at the ends of the treatment areas, and segmental devices typically have bone anchors at each adjacent bone segment.

There is a need for a segmental orthopaedic implant for spinal elongation and for treatment of scoliosis (the abnormal side-to-side curvature of a spine). Fusion instrumentation for scoliosis often consists of hooks, rods and screws of which pedicle screws are common. Hooks and screws are typically placed adjacent to the spinal facet joints. Fusion results in a loss of spinal mobility, loss of spinal growth and may aggravate spinal disc degeneration.

SUMMARY OF THE INVENTION

One embodiment of the invention relates to an orthopaedic device to realign bone segments. The orthopaedic device comprises a first attachment member attached to a first rib bone or first transverse process of a vertebra, a second attachment member attached to a second rib bone or second transverse process of a vertebra adjacent to the first rib bone or the first transverse process, and a spacer member positioned between the first and second attachment members. The spacer member provides distraction between the first and second rib bones or transverse processes to realign the rib bones.

Another embodiment of the invention relates to an orthopaedic device to realign bone segments. The orthopaedic device comprises a first attachment member attached to a first rib bone, first transverse process of a vertebra, or first lamina of a vertebra; a second attachment member attached to a second rib bone, second transverse process of a vertebra, or second lamina of a vertebra adjacent to the first rib bone, the first transverse process, or the first lamina; and a spacer member positioned between the first and second attachment members. The spacer member provides distraction between the first and second rib bones or transverse processes to realign the rib bones. The spacer member is releasably connected to the first and second attachment members.

Yet another embodiment of the invention relates to an attachment member for an orthopaedic device for realigning bone segments. The attachment member comprises a clamp to attach to a rib bone or transverse process of a vertebra. The clamp includes an upper arm, a lower arm, and a hinge. The attachment member further comprises a screw inserted into an opening in the clamp. The screw includes a screw head. The screw fixes into the rib bone or transverse process to prevent rotational movement or sliding of the clamp along the bone or transverse process.

Another embodiment of the invention relates to an orthopaedic device to realign bone segments. The orthopaedic device comprises a first attachment member attached to a first rib bone or first transverse process of a vertebra, a second attachment member attached to a second rib bone or second transverse process of a vertebra not adjacent to the first rib bone or the first transverse process, and a spacer member positioned between the first and second attachment members. The spacer member provides distraction between the first and second rib bones or transverse processes to realign the rib bones. The spacer member is releasably connected to the first and second attachment members.

It is to be understood that both the foregoing general description and the following detailed description are exemplary and explanatory only, and are not restrictive of the invention as claimed.

BRIEF DESCRIPTION OF THE DRAWINGS

Features, aspects, and advantages of embodiments of the present invention will become apparent from the following description, and the accompanying exemplary embodiments shown in the drawing, which is briefly described below.

FIG. 3(a) is a perspective view of an attachment member according to an embodiment. FIG. 3(b) illustrates a cross-sectional top view of the attachment member of FIG. 3(a) during attachment to a rib. FIG. 3(c) illustrates a cross-sectional side view of the attachment member of FIG. 3(a) prior to attachment to a rib. FIG. 3(d) illustrates a cross-sectional side view of the attachment member of FIG. 3(a) attached to a rib. FIG. 3(e) illustrates a front view of the attachment member of FIG. 3(a).

FIG. 4(a) is an exploded view of a clamp and screw prior to attachment to a cross-section of a rib in which a plate is attached to the screw and the clamp includes a wedge. FIG. 4(b) illustrates a side view of the attachment member of FIG. 4(a).

FIG. 6 illustrates a side view of first and second screws that each include plates according to another exemplary embodiment, in which a rod extends through the plates of the first and second screws.

FIGS. 7(a)-7(c) illustrate attachment members and a spacer member according to an exemplary embodiment. FIG. 7(a) illustrates an attachment member attached to a first rib and an attachment member attached to a second rib. FIG. 7(b) illustrates a spacer member attached to the attachment members of FIG. 7(a) in which the spacer member is in a shortened configuration. FIG. 7(c) illustrates a spacer member attached to the attachment members of FIG. 7(a) in which the spacer member is in a lengthened or expanded configuration.

FIG. 9(a) illustrates an orthopaedic device attached to adjacent ribs with a spacer member comprising a polymer matrix with a fabric housing attached to the attachment members according to an exemplary embodiment. FIG. 9(b) illustrates a perspective view of the fabric housing of FIG. 9(a).

FIGS. 10(a) and 10(b) illustrate screws of attachment members with a turnbuckle assembly according to another embodiment. FIG. 10(a) illustrates a threaded rod extending into passages of adjacent screws. FIG. 10(a) illustrates the threaded rod in a position different from FIG. 10(a).

DETAILED DESCRIPTION OF THE PREFERRED EMBODIMENTS

Figure 1A:
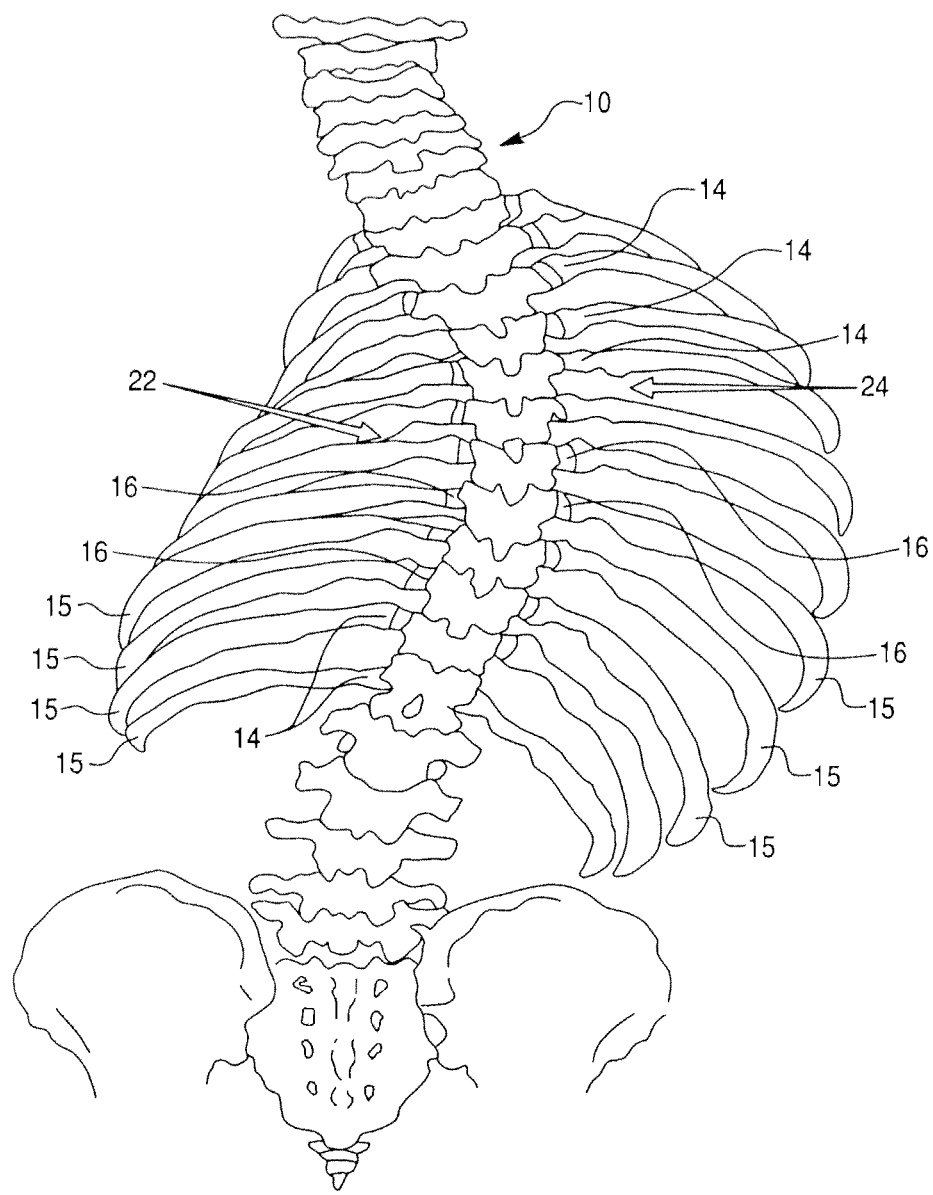
FIG. 1(a) illustrates a concave aspect of a scoliotic spine.

The disclosure relates to an orthopaedic device to realign bone segments. The orthopaedic device can have multiple components, each including attachment members to attach to bone and a spacer member, that allow segmental realignment of bone. The orthopaedic device can be anchored to adjacent segments of bone by attachment members and may be expanded via the spacer member to realign the bone segments. The attachment members alternate with the spacer members as will be understood from the FIGURES. The spacer members also may allow bending within themselves or at the connection between the spacer members and the attachment members.

In an exemplary embodiment, the orthopaedic device 100 may be used to treat and correct scoliosis, which is the side-to-side or lateral curvature of the spine 10. The orthopaedic device 100 also may be used to correct other orthopaedic and/or spinal defects.

The orthopaedic device 100 can provide a fusionless treatment for patients with scoliosis. This orthopaedic device 100 can be fusionless in the sense that it can differ from current treatment for advanced scoliosis, which straightens the spine with rigid instrumentation (combination of hooks, screws, and rods) and then requires spinal fusion that eliminates all mobility between the vertebral segments with the fused region. The orthopaedic device 100, according to embodiments of the invention, allows mobility between segments of the spine 10.

Known fusionless devices, such as a tether or staples, are placed on the vertebral bodies at the convexity 24 of the scoliotic spine 10 and seek to correct a deformity by tethering and attempting to arrest or slow spinal growth at the convex aspect (side) 24 of the spine 10. In contrast, the orthopaedic device 100, according to embodiments of the present disclosure, is placed at the concavity 22 of the scoliotic spine 10. Correction of the scoliosis is achieved by elongation of the orthopaedic device 100. This elongation is achieved by expansion or flexing of individual spacer (or expandable) members 150, and, according to an exemplary embodiment, such expansion occurs after all attachment members 110 and spacer members 150 are implanted.

Figure 2:
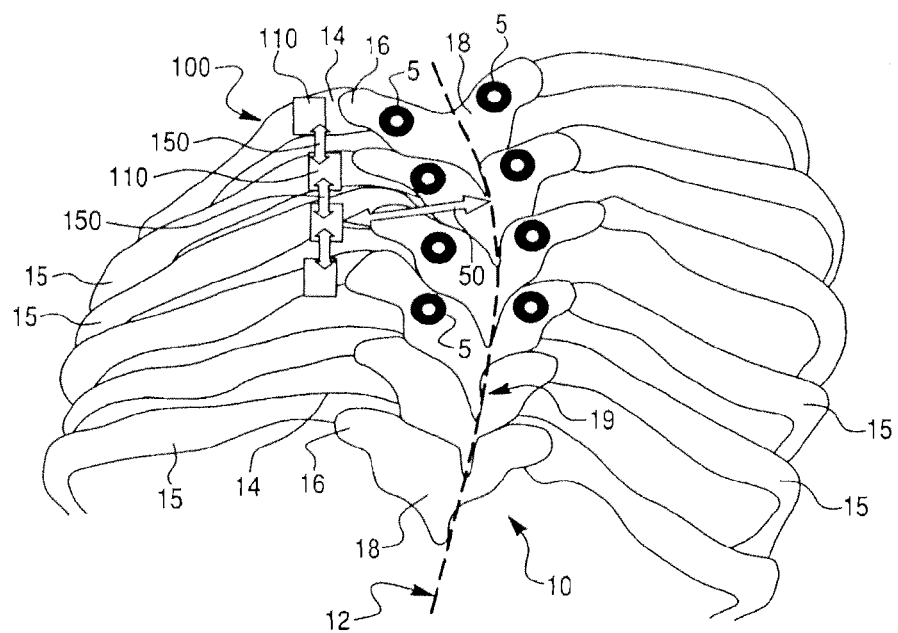
FIG. 2 illustrates a moment (or lever) arm that extends from a midline of the spine to an attachment member attached at a rib bone or transverse process.

According to an exemplary embodiment, the orthopaedic device 100 attaches to a lateral concave aspect 22 of the spine 10 or proximal rib bone 15 (such as the rib head 14). Alternatively, the attachment members 110 are attached to a lamina 19 of a vertebra (FIG. 2). The orthopaedic device 100 elongates over time (such as from minutes to days); the device 100 remains in an elongated position after implantation; and the device 100 is not entirely rigid. The elongation time can vary depending upon the specific spacer member 150 utilized.

The orthopaedic device 100 comprises first and second attachment members 110 that are configured to be attached to adjacent rib bones 15 or transverse processes 16, and a spacer member 150 positioned between the first and second attachment members 110. The spacer member 150 provides distraction between the first and second rib bones 15 or transverse processes 16 to realign the rib bones and ultimately the spine 10. The spacer member 150 can be expandable and/or flexible. Alternatively, the attachment members 110 are attached to non-adjacent rib bones 15 or transverse processes 16.

Figure 1B:
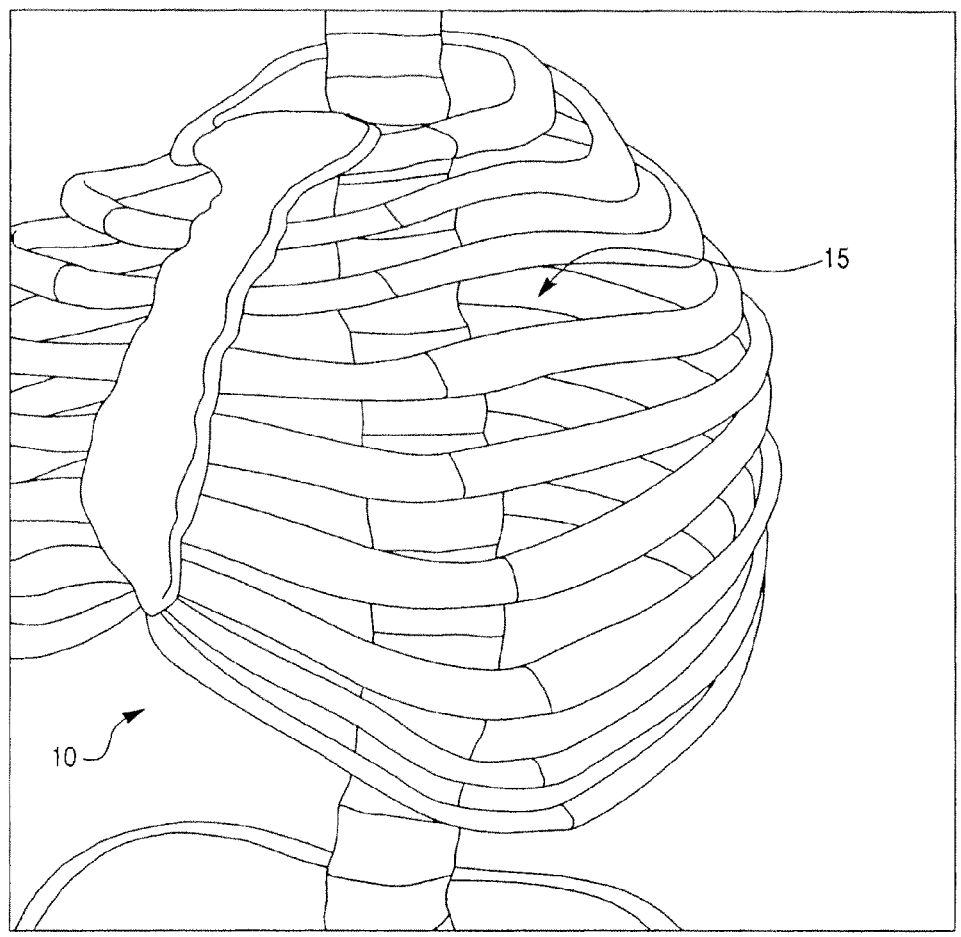
FIG. 1(b) illustrates an anterior oblique view of the spine.

The attachment members 110 of the orthopaedic device 100 can be attached to the lateral aspect of the spine 10 (such as the transverse process 16 or lamina 19) or proximal rib bone 15 just adjacent to the transverse process (such as near the rib head 14). The attachment members 110 can attach to the transverse process 16 of the vertebrae, rib bones 15, other regions of the vertebrae or bones on the appendicular skeleton. The device 100 is attached to the concave aspect 22 of the scoliotic curve so that, when the spacer members 150 expand, a corrective force is applied and straightening of the scoliosis occurs. The concave aspect 22 of the spine 10 is the inner or concave portion of the curved spine 10, such as shown in FIG. 1. According to an exemplary embodiment, the orthopaedic device 100 has multiple attachments to bone.

According to an exemplary embodiment shown in FIG. 2, the orthopaedic device 100 is positioned laterally from a midline 12 of the spine 10 to produce greater mechanical advantage by having a longer lever arm 50 such that correction of the deformity may be easier. The orthopaedic device 100 can be attached to a transverse process (which is lateral to the midline 12 of a spine 10) or along a rib bone 15 (such as at a rib head 14 or along a middle portion of the rib bone 15). For example, the attachment members 110 are configured to be attached to a proximal or middle portion of the rib bone 15. FIG. 2 illustrates a moment (or lever) arm 50 to a rib bone 15 from the axis of rotation, which for a spinal segment is approximately the midline 12 of the spine 10 at the spinal disc. Leverage is increased by attaching the orthopaedic device 100 at a proximal portion or middle portion of the rib bone 15. Mechanically, a greater corrective bending moment is produced with the longer lever arm 50 for a given distraction force produced by the spacer member 150. In other words, the orthopaedic device 100 is attached at a location that is lateral from the spinal vertebrae.

The spacer member 150, when positioned laterally from the spinal vertebrae, gives a longer lever arm 50 to move the rib bones 15 apart and correct the scoliotic curve of the spine 10. By having the attachment members 110 positioned laterally of the spine 10 (i.e., at a proximal or middle portion of the rib bones 15), a greater corrective force may be applied in the correction of the scoliotic spine.

In an exemplary embodiment, each spinal (or vertebral) level or segment has its own attachment member 110. Since the entire orthopaedic device 100 may be modular, the amount of expansion between each segment may be selected by the operating surgeon. The spacer members may be replaced without requiring removal of the associated attachment members. The spacer member 150 is releasably connected to the attachment members 110. The spacer member 150 is releasable because the spacer member 150 is configured to be removed from corresponding attachment members 110 while the corresponding attachment members remain in situ. The releasable connection is configured to allow for the spacer member 150 to be exchanged without requiring removal of corresponding attachment members 110. For example, the spacer member 150 can be removed without damaging the attachment members 110. A first spacer member 150 with a given force can be replaced with another spacer member 150 that provides a different corrective force. A spacer member 150 can also be exchanged for a different sized spacer member 150. For example, a shorter or longer spacer member 150 may be needed depending upon the current or desired spacing between rib bones 15.

According to an exemplary embodiment, the orthopaedic device 100 may be modular to allow for additional attachment members 110 and/or spacer members 150 to be placed or existing attachment members 110 and/or spacer members 150 to be exchanged for others of greater size for additional deformity correction. The attachment members 110 can be removed/released, for example, by unscrewing of the screw head 114.

In an exemplary embodiment, the orthopaedic device 100 may be modular in that its attachment 110 and/or spacer members 150 may be exchanged and/or replaced depending upon the needs of the patient. For example, if the desired spinal correction is not achieved or if additional correction is desired, the modular nature of the orthopaedic device 100 allows the surgeon to exchange spacer members 150 with different corrective forces and/or size either at the time of initial implantation or at a future date. By incrementally correcting the spinal deformity, or by staging the correction over multiple surgeries, the surgeon can minimize risk of spinal cord injury because the surgeon can avoid too much correction, with potential stretching of the spinal cord, in a single setting.

The screw 114 can be configured to connect to the rib bone 15, transverse process 16, or lamina 19. The screw 114 can include a screw head 115. The attachment members 110 can also include a nail instead of a screw 114.

In an exemplary embodiment, the orthopaedic device 100 includes multiple attachments to bone via a plurality of attachment members 110 attached to rib bones 15 or transverse processes 16. The attachment members 110 can include a clamp 120-screw 114 combination (shown in FIGS. 3(a)-3(e)), or other suitable combination to secure the attachment members 110 to the transverse process 16 or rib bone 15.

Figure 3A:
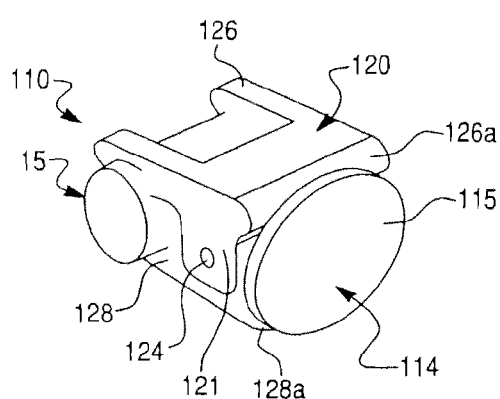
FIGS. 3(a)-3(e) illustrate an attachment member with a clamp/screw combination according to an exemplary embodiment.
Figure 3B:
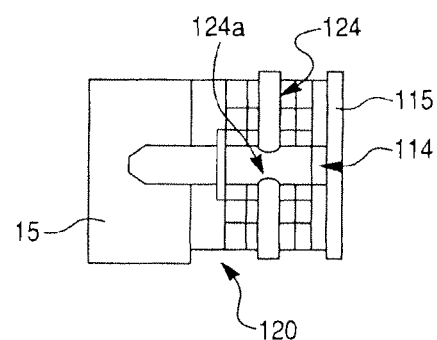
Figure 3C:
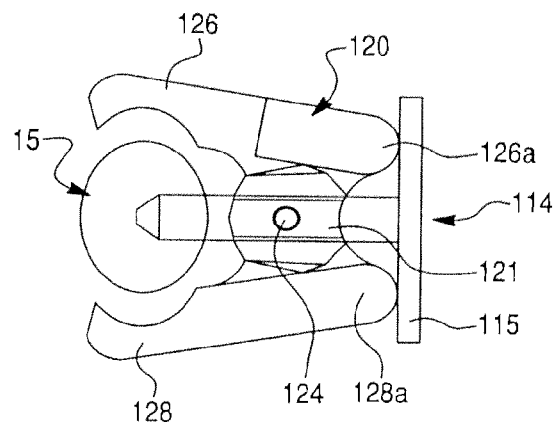
Figure 3D:
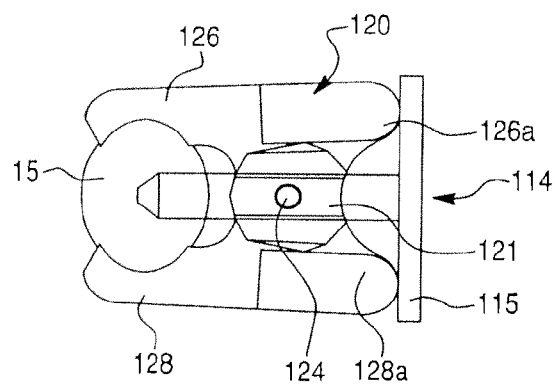
Figure 3E:
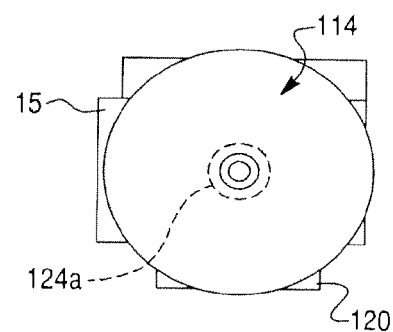

The clamp 120 can, for example, fit at least around a portion of a rib bone 15 or transverse process 16. The clamp 120 can include an upper arm 126 with a shoulder portion 126a, a lower arm 128 with a shoulder portion 128a, and a hinge 124 about which the arms 126, 128 pivot. The hinge 124 can include an opening 124a for the screw 114. As can be seen in FIG. 4(b), the screw 114 can be inserted through the opening 124a. Each arm 126, 128 can include shoulder portions 126a, 128a adjacent to a screw head 115 when the screw 114 is inserted through the clamp 120 and into the rib bone 15 or transverse process 16. The clamp 120 can include a lever arm portion 121, which is best shown in FIGS. 3(a), 3(c) and 3(d). As the upper 126 arm and lower arm 128 rotate about the hinge 124 toward each other into a clamped position (FIG. 3(d)), the lever arm portion 121 rotates. For example, in FIG. 3(c), the lever arm portion 121 is in a different position in an open (unclamped position) then when the clamp is in a clamped position about a rib bone 15, such as shown in FIG. 3(d).

The clamp 120 can move into a clamped position (FIG. 3(d)) by action of the screw 114. As the screw 114 is advanced through the clamp 120 and, thus, hinge 124 and hinge opening 124a, threads in the hinge opening 124(a) (not shown) correspond to and fit the screws on the screw 114. When the screw 114 is tightened into placement in the rib bone 15, the screw head 115 pushes against shoulders 126a, 128a of the upper arm 126 and lower arm 128. The pushing movement against the shoulders 126a, 128a is configured to rotate the upper arm 126 and lower arm 128 toward each other and into a clamped position. The shoulders 126a, 128a are offset from the hinge 124, the motion of the screw head 115 against the shoulders 126a, 128a forces the arms 126, 128 to clamp into a closed position.

Figure 4A:
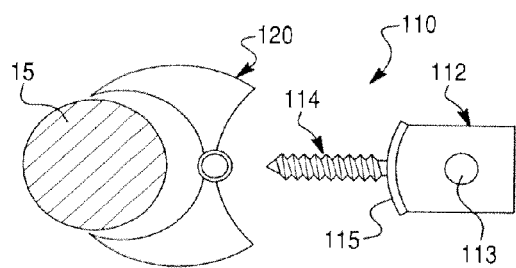
FIGS. 4(a) and 4(b) illustrate an attachment member according to another embodiment.
Figure 4B:
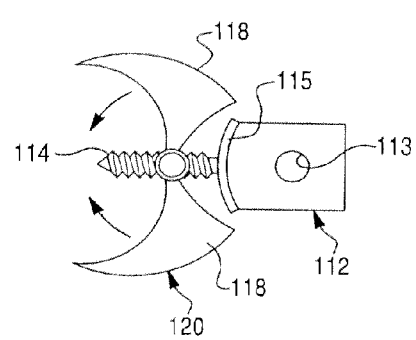

Referring to FIGS. 4(a) and 4(b), the clamp 120-screw 114 combination can include a wedge portion 118. The wedge portion 118 is connected to or integral with the clamp 120 and is adjacent to the clamp hinge 124. When the screw 114 is tightened, the screw 114 abuts the wedge portion 118, which levers the clamp 120 to tighten around the rib bone 15. As the screw head 15 is tightened, the screw head 15 pushes against the clamp 120 and wedge portion 118 to tighten the clamp 120 against the rib bone 15, thus moving the upper arm 126 and lower arm 128 toward each other into a clamped position.

Each attachment member 110 also includes a connector or connector member 112, such as shown in FIGS. 4(a) and 4(b), for seating a spacer member 150, such as shown in FIGS. 7(b) and 7(c). The connector member 112 can be connected to or integral with the screw head 115. The connector member 112 geometry can vary depending upon the particular spacer member 150; preferably the connector member is in the shape of a plate. In FIGS. 4(a) and 4(b), the connector member 112 can include an opening 113 to engage with a corresponding spacer member 150. The spacer member 150 can have a suitable geometry, such as a projection, to mate with and attach (preferably releasably) with the opening 113.

Figure 5A:
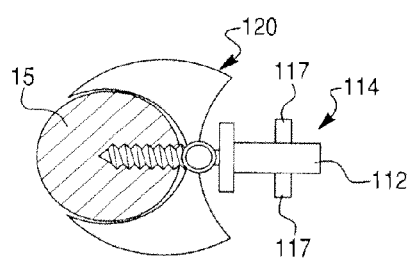
FIG. 5(a) illustrates a side view of an attachment member attached to a rib in which a plate includes a protrusion according to an exemplary embodiment.

Referring to FIG. 5(a), the clamp 120-screw 114 combination is shown in which the screw 114 includes a connector member 112 having protrusions 117 (or pegs) extending from opposite sides of the connector member 112. The protrusions 117 are provided to attach (preferably releasably) to a corresponding portion of a spacer member 150. For example, the protrusions 117 could extend into a corresponding hole in a spacer member 150.

Figure 5B:
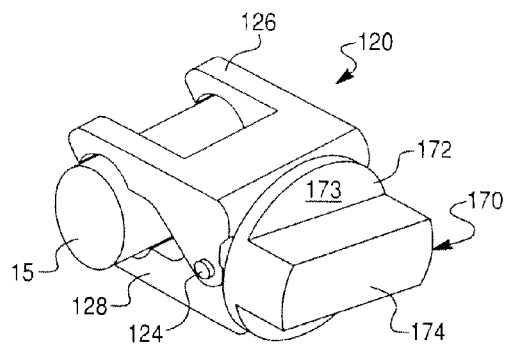
FIG. 5(b) is a perspective view of an attachment member according to another embodiment.
Figure 5C:
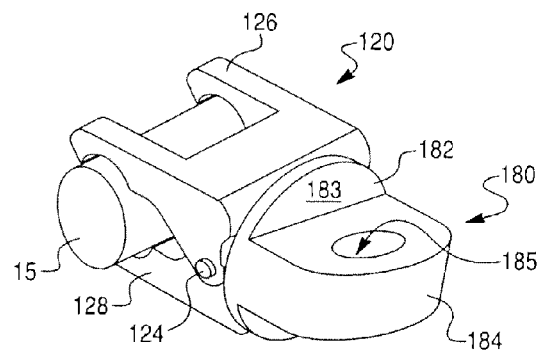
FIG. 5(c) is a perspective view of an attachment member according to another embodiment.
Figure 5D:
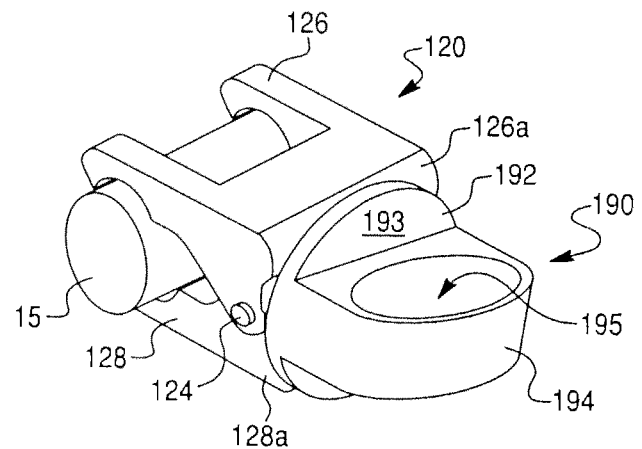
FIG. 5(d) is a perspective view of an attachment member according to another embodiment.
Figure 5E:
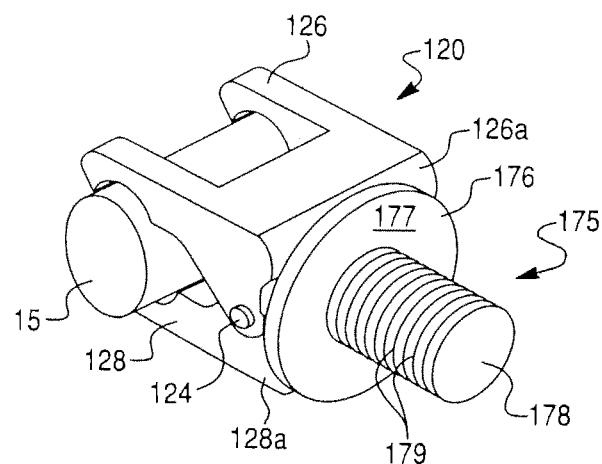
FIG. 5(e) is a perspective view of an attachment member according to another embodiment.

Referring to FIG. 5(b), a clamp 120-screw 170 combination is shown attached to a rib bone 15 according to another embodiment. In this embodiment, the screw 170 includes a screw head 172 with a geometry configured to couple with and releasably engage with a corresponding spacer member 150. The screw head 172 can include a generally rectangular protrusion or extension 174 that protrudes out from a top surface 173 of the screw head 172. For example, the protrusion 174 could extend into a corresponding hole in a spacer member 150. In an exemplary embodiment, the attachment member 110, such as the clamp 120-screw 170 combination of FIG. 5(b), does not extend all the way around a rib bone 15.

For example, the clamp 120 may attach only to opposite sides of the rib bone 15, but it need not encircle the rib bone 15. The clamp 120-screw 170 combination also is rotationally stable because the screw 170 prevents the clamp 120 from rotating around or sliding along the rib bone 15 despite the clamp 120 being non-circumferential. The screw 170 extends through a portion of the clamp 120 and tightens (screws) into the rib bone 15 or transverse process 16. The screw 170 can act as a barrier to rotational or sliding movement of the clamp 120 when screwed into the rib bone 15 or transverse process 16.

Referring to FIG. 5(*c*), a clamp 120-screw 180 combination is shown attached to a rib bone 15 according to another embodiment. In this embodiment, the screw 180 can include a screw head 182 with a rounded protrusion 184 extending from the screw head 182. The rounded protrusion 184 includes a hole or passage 185 for receiving an alignment member or rod 220 (see FIG. 6) or any other suitable connector component of a corresponding spacer member 150. As the rib bones 15 are realigned and move, the rod 220 is capable of sliding within the opening 220. The rod 220 may be rigid, flexible, or expandable and can span multiple spinal levels. The rod 220 may be coupled to (via another protrusion 184 and hole 185, or other suitable connection) to another attachment member 110 attached to a different rib bone 15 or transverse process 16.

Referring to FIG. 5(*d*), a clamp 120-screw 190 combination is shown attached to a rib bone 15 according to another embodiment. In this embodiment, the screw 190 can include a screw head 192 with a geometry configured to couple with and releasably engage with a corresponding spacer member 150. The screw head 192 can include a generally rounded protrusion or extension 194 that protrudes out from a top surface 193 of the screw head 192. The protrusion 194 can include a well 195 or opening that does not pass completely through the protrusion. The well 195 and protrusion 194 are configured to couple with a corresponding spacer member 150. For example, the well 195 could engage with a corresponding projection on the spacer member 150.

Referring to FIG. 5(*e*), a clamp 120-screw 175 combination is shown attached to a rib bone 15 according to another embodiment. In this embodiment, the screw 175 can include a screw head 176 with a geometry configured to couple with and releasably engage with a corresponding spacer member 150. The screw head 176 can include a threaded protrusion or peg 178 that protrudes out from a top surface 177 of the screw head 176. The protrusion 178 includes threads 179 that are configured to mate with corresponding threads on a spacer member 150.

Referring to FIG. 6, a screw 114 and connector member 212 are shown. The connector member 212 includes an opening (passage or channel) 214 for an alignment member or rod 220 to slide through. As the rib bones 15 are realigned and move, the rod 220 is capable of sliding within the opening 220. The rod 220 may be rigid, flexible, or expandable and can span multiple spinal levels. The rod 220 may be coupled to (via another connector member 212, or other suitable connection) to another attachment member 110 attached to a different rib bone 15 or transverse process 16. For example, FIG. 6 illustrates the rod 220 extending through two adjacent screws 114 and corresponding connector members 212. The rod 220 is configured to connect all attachment members 110 and can be used to align attachment points on rib bones 15. For example, the openings 220 on the connector members 212 of all attachment members 110 must all be sufficiently aligned such that the rod 220 can slide through all of the openings 220. The rod 220 can also help improve spinal growth by helping direct movement of the rib bones 15 by aligning the rib bones 15. The rod 220 is preferably unthreaded and is slidably positioned within all of the openings 220.

According to an exemplary embodiment, spacer members 150 may be positioned between attachment members 110 and result in the lengthening of the assembled orthopaedic device 100. The spacer members 150 may allow motion (bending or twisting or flexing) between the attachment members 110. The motion may be constrained so as to only allow bending in a single direction by selection of appropriate materials for the spacer member 150. For example, the spacer member 150 can comprise a polymer as described below.

Spacer members 150 are inserted at the time of surgery in a compressed form between adjacent attachment members 110. Once the entire orthopaedic construct is assembled, the spacer members 150 are allowed to expand, which gives correction to the deformity (see FIGS. 7(*b*) and 7(*c*)). FIGS. 7(*b*) and 7(*c*) generally show a spacer member 150 for explanatory purposes. The spacer members 150 not only expand longitudinally, but also may have some bending ability so as not to overly constrain the assembly and, thus, allow a small degree of spinal mobility. According to an exemplary embodiment, the orthopaedic device 100 initially is positioned in a bent form, such as shown in FIG. 7(*b*). When the spacer member 150 expands, the spacer member 150 straightens, such as shown in FIG. 7(*c*). The spacer member 150 can produce a corrective force of, for example, 50 to 200 N.

The spacer members 150 may be positioned posterior to or lateral to the attachment members 110. The spacer members 150 may also be anterior to the attachment members 110, such as when the device 100 is placed from an anterior approach to the rib heads 14 via the chest. Referring to FIG. 1(*b*), which illustrates the spine 10 from an anterior view, the attachment members 110 and spacer members 150 can be attached to the rib bones 15 from a frontal (anterior) approach that reverses the direction which the attachment members 110 and spacer members 150 face. In other words, if the screw head 115 faces towards a back-side of a patient with the orthopaedic device, the screw head 115 in the anterior position would face the front-side of the patent.

Figure 8:
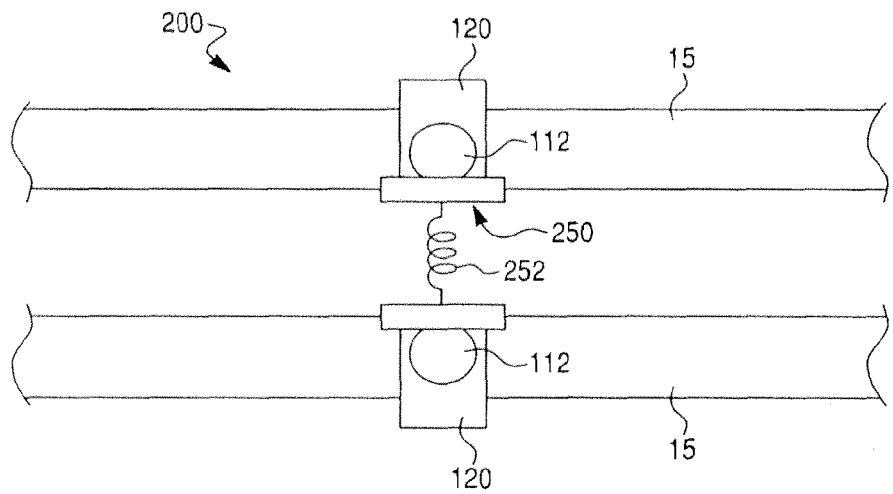
FIG. 8 illustrates an orthopaedic device attached to adjacent ribs with a spacer member comprising a spring attached to the attachment members according to an exemplary embodiment.

One possible type of spacer member 250 is a spring 252, such as shown in FIG. 8. The spring 252 may be a nitinol spring that is implanted between the attachment members 110 in a compressed state and then simultaneously expanded with those at other spinal segments. The spring 252 may be fabricated of nitinol or another suitable metal that can be induced to change shape or expand. The spring 352 may comprise a shape memory alloy. The spring 252 may be a coil spring.

Figure 9A:
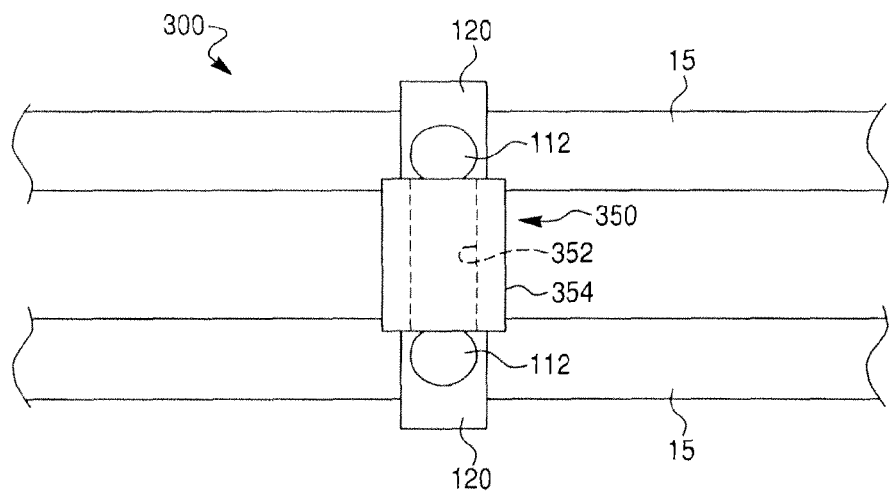
FIGS. 9(a) and 9B) illustrate a spacer member according to another embodiment.
Figure 9B:
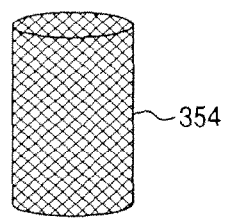

Referring to FIGS. 9(*a*) and 9(*b*), the spacer member 350 may be a polymer 352 in an alternative embodiment. The polymer 352 may be a hydrogel that can be induced to change shape or expand. For example, the polymer 352 may comprise a polyvinyl hydrogel. The spacer member 350 may be fabricated by certain polymeric hydrogels, which may be inserted in a dehydrated state and then expand as they absorb water from the surrounding muscle tissues that overlie the assembly after completion of the surgery. The polymer 352 may also include a housing 354. The housing 354 can be a fabric housing. The fabric housing 354 can comprise a wire mesh, such as shown in FIG. 9(*b*).

The spacer member 350, according to an exemplary embodiment, may have a composite with a reinforcing fiber pattern within the polymer matrix 352 to allow expansion in a preferential (e.g., longitudinal) direction.

Another type of spacer member 150 may be electromagnetic with a small motor (not shown). The electromagnetic motor may have a housing that expands in the presence of an applied magnetic field. The electromagnetic motor may incorporate a screw that elongates in the presence of an applied magnetic field which thus produces an elongation and distractive force between the attachment members 110.

In alternative embodiments, the spacer member 150 may include a threaded turnbuckle assembly, such as shown in FIGS. 10(a) and 10(b). The screw 114 includes a connector portion 412 with a passage or opening 414. The interior of the passage 414 is threaded to mate with threads on a threaded rod or member 420. The rod can extend between two or more attachment members 110 and is threadably attached to the connector portion 412. A nut 422 can be positioned on the threaded rod 420 adjacent to connector portion 412. The threaded rod 420 and connector portion 412 (turnbuckle assembly) can be adjusted to provide a distraction force by movement of the threaded rod 420 within the passages 414 of adjacent connector portions 412. The threaded rod 420 can be threaded into the passages 414 to have the connector portions 412 (and thus, attachment members 110 and attached rib bones 15) closer together, such as shown in FIG. 10(a). Unthreading the threaded rod 420 from the passages 414 can push the connector plates 412 apart to provide a distraction force on the associated rib bones 15.

Although the orthopaedic device 100 has been described as a fusionless device, according to another exemplary embodiment, the orthopaedic device 100 also may be used as a fusion device for internal fixation if combined with a bone-graft. For example, the device 100 can be used as a temporary splint or holding device to keep bones in a correct fused alignment/position until the bone graft is capable of fusing together the bones. When fusion of the bones is complete, the device 100 can be removed.

The FIGURES illustrate the clamp 120 attached to a rib bone 15, but it should be known that the clamp 120 could can also attach to a rib head 14, transverse process 16, lamina 19, or any other suitable location. According to an exemplary embodiment, the device 100 may be non-rigid and expandable.

The device 100 can also be made of a material that is biocompatible and/or include a biocompatible coating on the attachment members and/or spacer members to enhance fixation of the attachment members to bone comprised of a porous surface texture. The biocompatible coating/material can comprise, for example, hydroxyappetite.

Figure 11:
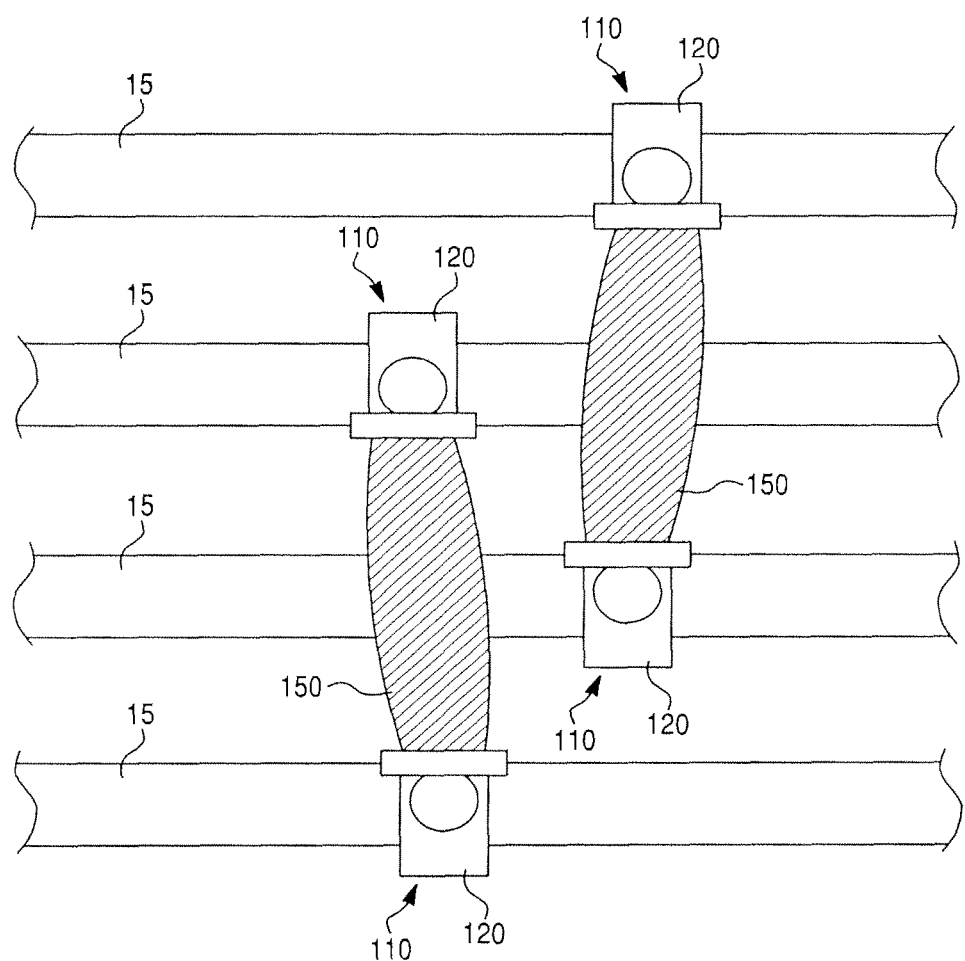
FIG. 11 illustrates orthopaedic devices with attachment members with connecting spacer members attached at non-adjacent rib bones.

Attachment members 110 may or may not be placed at every spinal level. In particular cases, the implanting surgeon may desire to skip a spinal level. The attachment members 110 may be used at any spinal level. For example, such as shown in FIG. 11 a first attachment member 110 can be attached to a first rib bone 15 and a second attachment member 110 can be attached to a second rib bone 15 not adjacent to the first rib bone 15. The spacer member 150 can be positioned between the first and second attachment members 110 to provide distraction between the first and second rib bones 15.

It is important to note that the construction and arrangement of the orthopaedic device as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosure herein. For example, elements shown as integrally formed may be constructed of multiple parts or elements, the position of elements may be reversed or otherwise varied, and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes and omissions may be made in the design, operating conditions and arrangement of the exemplary embodiments.

What is claimed is:

1. An attachment member for an orthopaedic device for realigning bone segments, the attachment member comprising:
   a clamp to attach to a rib bone, a lamina, or a transverse process of a vertebra, the clamp including an upper arm, a lower arm, and a hinge; and
   a screw inserted into an opening in the clamp, the screw including a screw head and a longitudinal axis that extends along a length of the screw, the screw configured to, upon tightening, advance through the opening in the clamp, to fix into the rib bone, the lamina, or the transverse process to prevent rotational movement or sliding of the clamp along the rib bone, the lamina, or the transverse process,
   wherein the upper arm includes a first shoulder having a first prominence and wherein the lower arm includes a second shoulder having a second prominence, the first prominence and the second prominence being positioned adjacent to the hinge such that as the screw is tightened to advance through the opening in the clamp to fix into the rib bone, the lamina, or the transverse process, the screw head pushes against the first prominence and the second prominence to force the upper and lower arms to pivot about the hinge to a clamped position,
   wherein the clamp includes a first clamp and the attachment member further comprises:
   a second clamp to attach to a second rib bone, a second lamina, or a second transverse process of a second vertebra, the second clamp including a second clamp upper arm, a second clamp lower arm, and a second clamp hinge, the second clamp upper arm and the second clamp lower arm including a third clamp shoulder and a fourth clamp should respectively, the third clamp shoulder and the further clamp shoulder including a third prominence and a fourth prominence respectively, the third prominence and the fourth prominence being positioned adjacent to the hinge;
   a second screw inserted into a second clamp opening in the second clamp, the second screw including a second screw head, a second longitudinal axis that extends along a length of the seconds screw, the second screw configured to, upon tightening, advance through the second clamp opening in the second clamp, to fix into the second rib bone, the second lamina, or the second transverse process to prevent rotational movement or sliding of the second clamp along the second rib bone, the second lamina, or the second transverse process; and
   a spacer member coupled to the first clamp and the second clamp.

2. The attachment member of claim 1, wherein the spacer member is expandable.

3. The attachment member of claim 1, wherein the spacer member is flexible.

4. The attachment member of claim 1, wherein the spacer member comprises a polymer.

5. The attachment member of claim 4, wherein the spacer member comprises a composite with a reinforcing tiber pattern within a polymer matrix.

6. The attachment member of claim 5, wherein the spacer member elongates in one direction.

7. The attachment member of claim 6, wherein the spacer member includes a fabric housing.

8. The attachment member of claim 7, wherein the spacer member comprises a wire mesh.

9. The attachment member of claim 1, wherein the spacer member comprises a spring.

10. The attachment member of claim 9, wherein the spring comprises a shape memory alloy.

11. The attachment member of claim 1, herein the first prominence and the second prominence include a wedge.

12. The attachment member of claim 1, wherein the attachment members comprise a biocompatible material to enhance fixation of the attachment members to the rib bones or transverse processes.

13. The attachment member of claim 12, wherein the biocompatible material comprises hydroxyapatite.

14. A method of attaching an orthopaedic device to at least one of a rib bone, a lamina, and a transverse process of a vertebra, the method comprising:
   clamping a clamp including an upper arm, a lower arm, and a hinge to the rib bone, lamina, or transverse process, the upper arm and the lower arm including a shoulder having a prominence positioned adjacent to the hinge;
   advancing a screw into an opening in the clamp, the screw including a screw head and a first longitudinal axis that extends along a length of the screw, such that as the screw is tightened to advance through the opening in the clamp the screw head pushes against the prominence to force the upper and lower arms to pivot toward one another into a clamped position; and
   fixing the screw into the at least one of the rib bone, the lamina, and the transverse process as the screw is advanced into the opening in the clamp to prevent rotational movement or sliding of the clamp along the at least one of the rib bone, the lamina, and the transverse process.

15. The method of attaching an orthopaedic device of claim 14, wherein the first clamp and the second clamp comprise a biocompatible material to enhance fixation of the first clamp and the second clamp to the rib bones or transverse processes.

16. The method of attaching an orthopaedic device of claim 15, wherein the biocompatible material comprises hydroxyapatite.

17. The method of attaching an orthopaedic device of claim 14, wherein the first clamp and the second clamp comprise a biocompatible coating to enhance fixation of the attachment members to the rib bones or transverse processes.

18. The method of attaching an orthopaedic device of claim 17, wherein the biocompatible coating comprises hydroxyapatite.

19. The method of attaching an orthopaedic device of claim 14, wherein the clamp includes a first clamp and wherein the method further comprises:
   clamping a second clamp to one of a second rib bone, lamina, and transverse process, the second clamp including a second clamp upper arm, a second clamp lower arm, and a second clamp hinge, the second clamp upper arm and the second clamp lower including second clamp shoulder including second clamp prominence positioned adjacent to the second clamp hinge;
   advancing a second screw into a second clamp opening in the second clamp, the second screw including a second screw head, a second longitudinal axis that extends along a length of the seconds screw, such that as the second screw is tightened to advance through the second clamp opening, the second screw head pushes against the second clamp prominence to force the second clamp upper and lower arms to pivot toward one another into a second clamped position;
   fixing the second screw into one of the second rib bone, lamina, and transverse process as the second screw is advanced into the first opening in the clamp to prevent rotational movement or sliding of the second clamp along the second rib bone, lamina, and transverse process; and
   coupling a spacer member to the first clamp and the second clamp.

* * * * *

UNITED STATES PATENT AND TRADEMARK OFFICE
CERTIFICATE OF CORRECTION

| | |
|---|---|
| PATENT NO. | : 9,204,899 B2 |
| APPLICATION NO. | : 14/444860 |
| DATED | : December 8, 2015 |
| INVENTOR(S) | : Glenn R Buttermann |

Page 1 of 1

It is certified that error appears in the above-identified patent and that said Letters Patent is hereby corrected as shown below:

IN THE CLAIMS
Col. 11, claim 5, line 2, "tiber" should be --fiber--.

Signed and Sealed this
Twenty-fourth Day of May, 2016

Michelle K. Lee
*Director of the United States Patent and Trademark Office*